(12) United States Patent
Blair et al.

(10) Patent No.: US 11,903,767 B2
(45) Date of Patent: *Feb. 20, 2024

(54) COMPOSITE TISSUE MARKERS DETECTABLE VIA MULTIPLE DETECTION MODALITIES

(71) Applicant: VIEW POINT MEDICAL, INC., Carlsbad, CA (US)

(72) Inventors: William Blair, San Diego, CA (US); Mike Jones, San Clemente, CA (US); John Merritt, San Clemente, CA (US)

(73) Assignee: VIEW POINT MEDICAL, INC., Carlsbad, CA (US)

(*) Notice: Subject to any disclaimer, the term of this patent is extended or adjusted under 35 U.S.C. 154(b) by 180 days.

This patent is subject to a terminal disclaimer.

(21) Appl. No.: 17/102,758

(22) Filed: Nov. 24, 2020

(65) Prior Publication Data
US 2021/0153845 A1    May 27, 2021

Related U.S. Application Data

(60) Provisional application No. 62/941,336, filed on Nov. 27, 2019.

(51) Int. Cl.
| | | |
|---|---|---|
| *A61B 8/08* | (2006.01) | |
| *A61B 6/00* | (2006.01) | |
| *A61B 90/00* | (2016.01) | |

(52) U.S. Cl.
CPC .............. *A61B 8/481* (2013.01); *A61B 6/481* (2013.01); *A61B 90/39* (2016.02); *A61B 2090/3908* (2016.02); *A61B 2090/3925* (2016.02); *A61B 2090/3966* (2016.02); *A61B 2090/3995* (2016.02)

(58) Field of Classification Search
CPC ..................................................... A61B 90/39
See application file for complete search history.

(56) References Cited

U.S. PATENT DOCUMENTS

| | | |
|---|---|---|
| 5,512,094 A | 4/1996 | Linton |
| 6,161,034 A | 12/2000 | Burbank et al. |
| 6,174,330 B1 | 1/2001 | Stinson |
| 6,221,326 B1 | 4/2001 | Amiche |

(Continued)

FOREIGN PATENT DOCUMENTS

| | | |
|---|---|---|
| CN | 102389576 A | 3/2012 |
| CN | 103803556 A | 5/2014 |

(Continued)

OTHER PUBLICATIONS

First Office Action dated Nov. 9, 2021 for CN201880023936.2, with translation, 24 pages.

(Continued)

*Primary Examiner* — Angela M Hoffa
*Assistant Examiner* — Younhee Choi
(74) *Attorney, Agent, or Firm* — Cozen O'Connor

(57) ABSTRACT

Aspects of the invention relate to composite markers that employ a gel carrier to carry two or more contrast materials, each detectable by a detection modality different than one another. Kits and methods for forming these composite markers and methods of marking a target site in a mammalian subject employing these composite markers are also discussed herein.

23 Claims, 3 Drawing Sheets

(56) References Cited

U.S. PATENT DOCUMENTS

| | | |
|---|---|---|
| 6,235,801 B1 | 5/2001 | Morales et al. |
| 6,331,166 B1 | 12/2001 | Burbank et al. |
| 6,347,241 B2 | 2/2002 | Burbank et al. |
| 6,427,081 B1 | 7/2002 | Burbank et al. |
| 6,494,841 B1 | 12/2002 | Thomas et al. |
| 6,567,689 B2 | 5/2003 | Burbank et al. |
| 6,699,206 B2 | 3/2004 | Burbank et al. |
| 6,725,083 B1 | 4/2004 | Burbank et al. |
| 6,862,470 B2 | 3/2005 | Burbank et al. |
| 6,996,433 B2 | 2/2006 | Burbank et al. |
| 7,322,938 B2 | 1/2008 | Burbank et al. |
| 7,322,939 B2 | 1/2008 | Burbank et al. |
| 7,322,940 B2 | 1/2008 | Burbank et al. |
| 7,651,505 B2 | 1/2010 | Lubock et al. |
| 7,792,569 B2 | 9/2010 | Burbank et al. |
| 7,871,438 B2 | 1/2011 | Corbitt |
| 7,970,454 B2 | 6/2011 | Jones et al. |
| 7,983,734 B2 | 7/2011 | Jones et al. |
| 8,157,862 B2 | 4/2012 | Corbitt |
| 8,177,792 B2 | 5/2012 | Lubock et al. |
| 8,219,182 B2 | 7/2012 | Burbank et al. |
| 8,224,424 B2 | 7/2012 | Burbank et al. |
| 8,361,082 B2 | 1/2013 | Jones et al. |
| 8,440,229 B2 | 5/2013 | Trogler et al. |
| 8,498,693 B2 | 7/2013 | Jones et al. |
| 8,626,269 B2 | 1/2014 | Jones et al. |
| 8,626,270 B2 | 1/2014 | Burbank et al. |
| 8,668,737 B2 | 3/2014 | Corbitt |
| 8,680,498 B2 | 3/2014 | Corbitt et al. |
| 8,718,745 B2 | 5/2014 | Burbank et al. |
| 8,784,433 B2 | 7/2014 | Lubock et al. |
| 8,880,154 B2 | 11/2014 | Jones et al. |
| 9,044,162 B2 | 6/2015 | Jones et al. |
| 9,149,341 B2 | 10/2015 | Jones et al. |
| 9,220,585 B2 | 12/2015 | Horton et al. |
| 9,327,061 B2 | 5/2016 | Govil et al. |
| 9,480,554 B2 | 11/2016 | Corbitt |
| 9,579,077 B2 | 2/2017 | Casanova et al. |
| 9,743,909 B1 | 8/2017 | Sapozhnikov et al. |
| 9,801,688 B2 | 10/2017 | Jones et al. |
| 9,820,824 B2 | 11/2017 | Jones et al. |
| 9,861,294 B2 | 1/2018 | Jones et al. |
| 10,172,674 B2 | 1/2019 | Jones et al. |
| 2003/0204137 A1 | 10/2003 | Chesbrough et al. |
| 2004/0116806 A1 | 6/2004 | Burbank et al. |
| 2004/0187524 A1 | 9/2004 | Sen et al. |
| 2004/0236213 A1 | 11/2004 | Jones et al. |
| 2005/0008578 A1 | 1/2005 | Schmidt |
| 2005/0063908 A1* | 3/2005 | Burbank ............ A61M 37/0069 424/9.5 |
| 2005/0158390 A1 | 7/2005 | Rana et al. |
| 2006/0079597 A1 | 4/2006 | Muratoglu et al. |
| 2006/0293581 A1 | 12/2006 | Plewes et al. |
| 2007/0276252 A1 | 11/2007 | Kolasa et al. |
| 2008/0097207 A1 | 4/2008 | Cai |
| 2011/0196285 A1 | 8/2011 | Chen et al. |
| 2011/0229576 A1 | 9/2011 | Trogler et al. |
| 2012/0052012 A1 | 3/2012 | Chenite et al. |
| 2012/0059376 A1 | 3/2012 | Rains et al. |
| 2013/0039848 A1 | 2/2013 | Bradbury et al. |
| 2013/0066195 A1 | 3/2013 | Sirimanne et al. |
| 2013/0230570 A1 | 9/2013 | Trogler et al. |
| 2014/0017130 A1 | 1/2014 | Trogler et al. |
| 2014/0187911 A1 | 7/2014 | Bolan et al. |
| 2014/0243675 A1 | 8/2014 | Burbank et al. |
| 2015/0057546 A1 | 2/2015 | Yoon et al. |
| 2015/0143688 A1 | 5/2015 | Garbini et al. |
| 2015/0173848 A1 | 6/2015 | Bolan et al. |
| 2015/0273061 A1 | 10/2015 | Trogler et al. |
| 2016/0051337 A1 | 2/2016 | Bolan et al. |
| 2016/0143624 A1 | 5/2016 | Liberman et al. |
| 2016/0151124 A1* | 6/2016 | Domb ................ A61L 31/18 600/431 |
| 2016/0346404 A1 | 12/2016 | Trogler et al. |
| 2017/0066162 A9 | 3/2017 | Fisher |
| 2017/0209601 A1 | 7/2017 | Kumar et al. |
| 2017/0368209 A1 | 12/2017 | Alqathami |
| 2018/0021102 A1 | 1/2018 | Azizian et al. |
| 2018/0065859 A1 | 3/2018 | Kummel et al. |
| 2018/0092987 A1 | 4/2018 | Trogler et al. |
| 2018/0280111 A1 | 10/2018 | Parish |
| 2018/0289444 A1 | 10/2018 | Blair et al. |
| 2019/0176372 A1 | 6/2019 | Fisher et al. |
| 2019/0192253 A1 | 6/2019 | Yang et al. |
| 2019/0365345 A1 | 12/2019 | Byram et al. |

FOREIGN PATENT DOCUMENTS

| | | |
|---|---|---|
| CN | 105377243 A | 3/2016 |
| JP | 2013536024 A | 9/2013 |
| JP | 2016505475 A | 2/2016 |
| JP | 2016516729 A | 6/2016 |
| JP | 6898603 B2 | 6/2021 |
| KR | 20150063097 A | 6/2015 |
| WO | 0110302 A3 | 8/2001 |
| WO | 2006105353 A2 | 10/2006 |
| WO | 2009023697 A2 | 2/2009 |
| WO | 2012142625 A2 | 10/2012 |
| WO | 2014052911 A1 | 4/2014 |
| WO | 2016149711 A1 | 9/2016 |
| WO | 2018097891 A1 | 5/2018 |
| WO | 2018187594 A2 | 10/2018 |
| WO | 2019067441 A1 | 4/2019 |
| WO | 2019243419 A1 | 12/2019 |

OTHER PUBLICATIONS

Hu et al., "Facile synthesis of amino-functionalized hollow silica microspheres and their potential application for ultrasound imaging, He Hu et al," Journal of Colloid and Interface Science, vol. 358, pp. 392-398, 2011.

Lu et al., "Synthesis of hollow silica microspheres and their applications in ultrasound imaging", Journal of Shanghai Normal University, vol. 41, Issue 4, pp. 432-439, 2012.

Notice of Reasons for Rejection, issued in corresponding Japanese Application No. 2021-063419, dated Apr. 11, 2022, 4 pages (English Translation).

Non Final Office Action for U.S. Appl. No. 17/102,761, dated Jun. 24, 2022, 20 pages.

Kamaya et al., Twinkling artifact on color Doppler sonography: dependence on machine parameters and underlying cause, AJR Am J Roentgenol. Jan. 2003; 180(1):215-22. doi: 10.2214/ajr.180.1. 1800215. (Year: 2003).

Arnal, Pablo M, et al., "High-temperature-stable catalysts by hollow sphere encapsulation," Angew Chem Int Ed Engl. Dec. 4, 2006;45(48):8224-7.

Brinker, C.J., "Hydrolysis and Condensation of Silicates: Effects on Structure", Journal of Non-Crystalline Solids, vol. 100, 1988, pp. 31-50.

Bunker, Christopher E, et al., "Low-Temperature Stability and High-Temperature Reactivity of Iron-Based Core-Shell Nanoparticles", J. Am. Chem. Soc., 2004, vol. 126, No. 35, pp. 10852-10853.

Caruntu, Daniela , et al., "Synthesis of Variable-Sized Nanocrystals of Fe304 with High Surface Reactivity," Chemistry of Materials, vol. 16(25), pp. 5527-5534. (Year: 2004).

Caruso, Frank , et al., "Electrostatic Self-Assembly of Silica Nanoparticle-Polyelectrolyte Multilayers on Polystyrene Latex Particles," J. Am. Chem. Soc., 1998, 120 (33), pp. 8523-8524.

Caruso, Frank , et al., "Magnetic Nanocomposite Particles and Hollow Spheres constructed by a Sequential Layering Approach." Chemistry of Materials, vol. 13, pp. 109-116. (Year: 2001).

Caruso, Frank , et al., "Nanoengineering of Inorganic and Hybrid Hollow Spheres by Colloidal Templating," Science Nov. 6, 1998: vol. 282, Issue 5391, pp. 1111-1114.

Cha, Jennifer N, et al., "Biomimetic synthesis of ordered silica structures mediated by block copolypeptides", Nature, vol. 403, Issue 6767, pp. 289-292 (2000).

Chang, Song-Yuan , et al., "Preparation and Properties of Tailored Morphology, Monodisperse Colloidal Silica-Cadmium Sulfide Nanocomposites,", J. Am. Chem. Soc., Jul. 1994, 116 (15), pp. 6739-6744.

(56) References Cited

OTHER PUBLICATIONS

Cornelissen, Jeroen J.L.M, et al., "Versatile synthesis of nanometer sized hollow silica spheres," Chem. Commun., 2003,8, 1010-1011.
Ding, Xuefeng, et al., "A novel approach to the synthesis of hollow silica nanoparticles," Materials Letters 2004, 58(27-28), 3618-3621.
Huang, Chih-Chia, et al., "Shell-by-shell synthesis of multi-shelled mesoporous silica nanospheres for optical imaging and drug delivery", Biomaterials, 32, 556-564,. (Year: 2011).
Jin, Pu, et al., "Synthesis and catalytic properties of nickel-silica composite hollow nanospheres." J Phys Chem B. May 1, 2004;108(20):6311-4. doi: 10.1021/jp049754g.
Kato, Noritaka, et al., "Synthesis of monodisperse mesoporous silica hollow microcapsules and their release of loaded materials." Langmuir. Sep. 7, 2010:26(17):14334-44. doi: 10.1021/la1024636.
Kempen, Paul J, et al., "Theranostic Mesoporous Silica Nanoparticles Biodegrade after Pro-Survival Drug Delivery and Ultrasound/Magnetic Resonance Imaging of Stem Cells." Theranostics 2015: 5(6) 631-642.
Lee, Jeongwoo, et al., "Synthesis of polystyrene/silica composite particles by soap-free emulsion polymerization using positively charged colloidal silica." J Colloid Interface Sci. Jun. 2007 A181;310(1):112-20. Epub Feb. 15, 2007.
Li, Xin, et al., "Formation of Gold Nanostar-Coated Hollow Mesoporous Silica for Tumor Multimodality Imaging and Photothermal Therapy", 5817-5827.
Liberman, Alexander, et al., "Color Doppler Ultrasound and gamma imaging of intratumorally injected 500nm iron-silica nanoshells" ACS Nano, Jul. 23, 2013, 7(7) 6367-6377.
Liberman, Alexander, et al., "Hollow iron-silica nanoshells for enhanced high intensity focused ultrasound" J Surg Res, May 10, 2014, 190(2): 391-398.
Liberman, Alexander, et al., "Mechanically tunable hollow silica ultrathin nanoshells for ultrasound contrast agents" Adv Funct Mater, 25(26) 4049-4057, May 21, 2015.
Liu, Jian, et al., "From Hollow Nanosphere to Hollow Microsphere: Mild Buffer Provides Easy Access to Tunable Silica Structure," J. Phys. Chem. C 2008, 112(42), pp. 16445-16451.
Lu, Yu, et al., "Synthesis and crystallization of hybrid spherical colloids composed of polystyrene cores and silica shells," Langmuir, American Chemical Society, 2004, pp. 3464-3470, vol. 20, No. 8.
Mallery, Susan R., et al., Mallery, Susan R. Mallery et al. Formulation and In-Vitro and In-Vivo Evaluation of a Mucoadhesive Gel Containing Freeze Dried Black Raspberries: Implications for Oral Cancer Chemoprevention, Pharma Res. 24(4), 728-737. (Year: 2007).
Martinez, Paul H, et al., Martinez et al., "Hard shell gas-filled contrast enhancement particles for colour Doppler ultrasound imaging of tumors" Medchemcomm, Oct. 2010 1(4) 266-270.
Mitchell, et al., "Iron(III)-Doped, Silica Nanoshells: A Biodegradable Form of Silica" J.Am. Chem. Soc. 2012, 34, 13997-14003 (Year: 2021).
Mori, Hideharu, et al., "Organic-Inorganic Nanoassembly Based on Complexation of Cationic Silica Nanoparticles and Weak Anionic Polyelectrolytes in Aqueous and Alcohol Media," Langmuir, vol. 20(5), 2004, pp. 1934-1944.
Nandiyanto, Asep Bayu Dani, et al., "Mesopore-Free Hollow Silica Particles with Controllable Diameter and Shell Thickness Via Additive-Free Synthesis." Langmuir. Jun. 12, 2012;28(23):8616-24. doi: 10.1021/la301457v. Epub May 31, 2012.
Paefgen, Vera, "Evolution of contrast agents for ultrasound imaging and ultrasound-mediated drug delivery," Front Pharmacol 2015, 6, 197.
Parida, Sudam K, et al., "Adsorption of organic molecules on silica surface," Advances in Colloid and Interface Science, 2006, vol. 121, Issue: 1-3, pp. 77-110.
Slowing, Igor I, et al., . "Mesoporous Silica Nanoparticles for Drug Delivery and Biosensing Applications," Adv. Funct. Mater., vol. 17, Issue Apr. 8, 2007 pp. 1225-1236.
Su, Yang, et al., "Synthesis of hierarchical hollow silica microspheres containing surface nanoparticles employing the quasi-hard template of poly(4-vinylpyridine) microspheres." Langmuir. Jul. 19, 2011;27 (14):8983-9. doi: 10.1021/la2014573. Epub Jun. 23, 2011.
Ta, Casey N., et al., "Integrated processing of contrast pulse sequencing ultrasound imaging for enhanced active contrast of hollow gas filled silica nanoshells and microshells," J. Vac. Sci. Technol. B 30(2), Mar./Apr. 2012, 6 pages.
Tada, Dayane B, et al., "Methylene Blue-Containing Silica-Coated Magnetic Particles: A Potential Magnetic Carrier for Photodynamic Therapy", Langmuir, 23, 8194-8199. (Year: 2007).
Tissot, Isabelle, et al., "Hybrid Latex Particles Coated with Sillca," Macromolecules, Jun. 7, 2001, 34 (17), pp. 5737-5739.
Van Bommel, Kjeld J.C, et al., "Poly(L-lysine) Aggregates as Templates for the Formation of Hollow Silica Spheres," Adv. Mater. vol. 13, Issue 19, Oct. 2001, pp. 1472-1476.
Velikov, Krassimir P, et al., "Synthesis and Characterization of Monodisperse Core-Shell Colloidal Spheres of Zinc Sulfide and Silica," Langmuir, Jul. 10, 2001, 17 (16), pp. 4779-4786.
Voss, R.K., "Doppler Ultrasound-Visible Signal Mark Microspheres are Better Identified than HydroMARK® Clips in a Simulated Intraoperative Setting in Breast and Lung Cancer," Presented at Society of Surgical Oncology meeting Chicago Illinois, Mar. 21-24, 2018.
Wang, H., "Spherical silicon-shell photonic band gap structures fabricated by laser-assisted chemical vapor deposition," J. Appl. Phys. 2007, 101, 033129, Published Online: Feb. 15, 2007 Accepted: Dec. 2006.
Ward, Erin, et al., "Utilization of Iron (III) Doped Nanoshells for in vivo Marking of Non-palpable Tumors using VX2 Rabbit Model." Am. J. Surg., Dec. 2016, 212(6): 1140-1146.
Wu, Dazhen, et al., "Novel One-Step Route for Synthesizing CdS/Polystyrene Nanocomposite Hollow Spheres," Langmuir May 26, 2004, 20, (13), pp. 5192-5195.
Wu, W., et al., "Synthesis of magnetic hollow silica using polystyrene bead as a template." Journal of Magnetism and Magnetic Materials, vol. 311(2), pp. 578-582, available online Sep. 22, 2006.
Xu, Xiangling, et al., "Synthesis and utilization of monodisperse hollow polymeric particles in photonic crystals" J Am Chem Soc. Jun. 4, 2004;126(25):7940-5.
Yao, Hiroshi, et al., "Electrolyte Effects on CdS Nanocrystal Formation in Chelate Polymer Particles: Optical and Distribution Properties", Langmuir 1998, 14(3), 595-601.
Yildirim, Adem, et al., "Stable Encapsulation of Air in Mesoporous Silica Nanoparticles: Fluorocarbon-Free Nanoscale Ultrasound Contrast Agents," Adv Healtho Mater. Jun. 2016; 5(11): 1290-1298.
Zhang, Kun, et al., "Double-scattering/reflection in a Single Nanoparticle for intensified Ultrasound Imaging," Sci Rep, 2015 5:8766.
Zhong, Ziyi, et al., "Preparation of mesoscale hollow spheres of TiO2 and SnO2 by templating against crystalline arrays of polystyrene beads," Adv. Mater. 2000, 12(3), 206-209.
Zhou, W., et al., "Drug-loaded, magnetic, hollow silica nanocomposites for nanomedicine." Nanomedicine: Nanotechnology, Biology and Medicine, vol. 1(3),2005, pp. 233-237.
Zhou, Dejian, et al., "Influence of the Foundation Layer on the Layer-by-Layer Assembly of Poly-L-lysine and Poly (styrenesulfonate) and Its Usage in the Fabrication of 3D Microscale Features." Langmuir, vol. 20(21), 2004, pp. 9089-9094.
Zhu, Yufang, et al., "Stimuli-responsive controlled drug release from a hollow mesoporous silica sphere/polyelectrolyte multilayer core-shell structure," Angew Chem Int Ed Engl. Aug. 12, 2005;44(32):5083-7.
European Search Report issued in European Application No. 18781390.2, dated Jan. 19, 2021, 8 pages.
Gorsd, Marina N. et al., "Synthesis and characterization of hollow silica spheres", Procedia Material Science, 2015, vol. 8, pp. 567-576.
International Preliminary Report on Patentability dated Feb. 16, 2010 in International Application No. PCT/US2008/072972 filed: Aug. 13, 2008 and published as: WO 2009/023697 on Feb. 19, 2009, 7 pages.
International Preliminary Report on Patentability dated Mar. 1, 2016 in International Application No. PCT/US2014/052911 filed: Aug. 27, 2014 and published as: WO 2015/031482 on Mar. 1, 2015, 9 pages.

(56) References Cited

OTHER PUBLICATIONS

International Preliminary Report on Patentability dated Sep. 19, 2017 in International Application No. PCT/US2016/023492 filed: Mar. 21, 2016 and published as: WO 2016/149711 on Sep. 22, 2016, 6 pages.
International Search Report & Written Opinion issued in Application No. PCT/US2020/048023, dated Dec. 9, 2020, 17 pages.
International Search Report and Written Opinion dated Aug. 16, 2016 in International Application No. PCT/US2016/023492 filed: Mar. 21, 2016 and published as: WO 2016/149711 on Sep. 22, 2016, 9 pages.
International Search Report and Written Opinion dated Dec. 3, 2018 in International Application No. PCT/US2018/026291 filed: April, 5, 2018 and published as: WO/2018/187594 on: Oct. 11, 2018.
International Search Report and Written Opinion dated Feb. 19, 2009 in International Application No. PCT/US2008/072972 filed: Aug. 13, 2008 and published as: WO 2009/023697 on Feb. 19, 2009, 9 pages.
International Search Report and Written Opinion dated Oct. 3, 2015 in International Application No. PCT/US2014/052911 filed: Aug. 27, 2014 and published as: WO 2015/031482 on Mar. 5, 2015, 14 pages.
International Search Report and Written Opinion, dated Apr. 6, 2021 2021, in International Application No. PCT/US2020/062322, 20 pages.
International Search Report and Written Opinion, dated Mar. 24, 2021, in International Application No. PCT/US2020/062272, 12 pages.
Office Action issued in Japanese Patent Application No. 2019-555229, dated Dec. 24, 2020, 8 pages.
Final Office Action dated Dec. 23, 2022, for U.S. Appl. No. 17/102,761, 22 pages.
Extended EP Search Report dated Nov. 17, 2022, EP App No. 20891874.8-1122, 7 pages.
Extended European Search Report for 20891745.0, dated Nov. 17, 2022, 8 pages.
EP Search Report dated Jul. 20, 2023 EP App No. 20857267-1126/4021306 PCT/US2020048023, 10 pages.
Richard Barr et al: "Artifiacts in diagnostic ultrasound, Reports in Medical Imaging", Jun. 1, 2013, p. 29, xp0555514374, DOI: 10.2147/RMI.S33464, pp. 41-42.

* cited by examiner

COMPOSITE TISSUE MARKERS DETECTABLE VIA MULTIPLE DETECTION MODALITIES

TECHNICAL FIELD

This disclosure generally relates to the field of tissue markers and detection of tissue markers, and in particular to composite tissue markers comprising a gel carrier carrying two or more different contrast materials.

BACKGROUND

Description of the Related Art

Various types of tissue markers exist for identifying, locating, and marking bodily tissues over time and for assisting in the biopsy, excision, or ablation of the marked bodily tissue. Current diagnostic and therapeutic protocols, including cancer diagnostic and treatment (e.g., surgical procedures, radiation treatment), are impeded by existing tissue marker technology for localization of lesions. For instance, in clinical settings, a tissue lesion of interest may be efficiently imaged and marked by radiologic markers during diagnostic stage, but these radiologic markers are not visible to surgeons intraoperatively in all surgical scenarios. As another example, fluorescent dye markers have been used widely in biomedical diagnosis and imaging. However, a typical fluorescent dye, such as indocyanine green, still suffers from major limitations for its utilization as a tissue marker in vivo due to its fast clearance, concentration-dependent aggregation, rapid protein binding, and bleaching effect due to various physicochemical attributes. Other difficulties may arise when the detection modality available for a particular clinical procedure is not compatible with the type of tissue being detected. For instance, lung tissue is porous with a high density of air to tissue interfaces, which interfere with ultrasound energy propagation.

Therefore, there remains a continuing need in the art to develop a simplified yet versatile and durable solution to tissue markers that are detectable via multiple detection modalities, retain and preserve the detectability of each marker element in the tissue marker, and persist in the tissues over a suitable time period.

SUMMARY

In at least one aspect, a composite marker may be summarized as comprising a plurality of ultrasound reflective elements; at least one contrast material detectable via a detection modality different than ultrasound imaging; and a gel carrier. Each ultrasound reflective element respectively comprises a body having at least one cavity and at least one fluid in the at least one cavity to provide reflectivity of ultrasound imaging signals. The at least one contrast material is not included in an outer layer of each ultrasound reflective element. The ultrasound reflective element and the at least one contrast material are carried in or on the gel carrier.

In another aspect, a composite marker may be summarized as comprising an activated and/or hydrolyzed fluorescent dye; at least one contrast material detectable by a detection modality different than detection of fluorescence; and a gel carrier. The activated and/or hydrolyzed fluorescent dye and the at least one contrast material are carried in or on the gel carrier.

In yet another aspect, a kit for forming a composite marker may be summarized as comprising a plurality of ultrasound reflective elements; at least one contrast material detectable via a detection modality different than ultrasound imaging; and a gel or gel forming material. Each ultrasound reflective element respectively comprises a body having at least one cavity and at least one fluid in the at least one cavity to provide reflectivity of ultrasound imaging signals. The at least one contrast material is not included in an outer layer of each ultrasound reflective element. When being mixed with the plurality of ultrasound reflective elements and the at least one contrast material, the gel or gel forming material results in a gel carrier which carries the plurality of ultrasound reflective elements and the at least one contrast material in or on the gel carrier to form a composite marker.

In yet another aspect, a kit for forming a composite marker may be summarized as comprising a fluorescent dye; at least one contrast material detectable by a detection modality different than detection of fluorescence; and a gel or gel forming material. When being mixed with the at least one contrast material and the fluorescent dye, the gel or gel forming material results in a gel carrier which carries the at least one contrast material and the fluorescent dye in or on the gel carrier to form a composite marker.

In at least one aspect, a method for forming a composite marker may be summarized as comprising mixing 1) a plurality of ultrasound reflective elements, each ultrasound reflective element respectively comprising a body having at least one cavity and at least one fluid in the at least one cavity to provide reflectivity of ultrasound imaging signals; 2) at least one contrast material detectable by a detection modality different than ultrasound imaging, wherein the at least one imaging material is not included in an outer layer of each ultrasound reflective element; and 3) a gel or gel forming material, to result in a gel carrier carrying the plurality of ultrasound reflective elements and the at least one contrast material in or on the gel carrier to form a composite marker.

In at least one aspect, a method for forming a composite marker may be summarized as comprising mixing 1) a fluorescent dye; 2) at least one contrast material detectable by a detection modality different than detection of fluorescence; and 3) a gel or gel forming material, to result in a gel carrier carrying the fluorescent dye and the at least one contrast material in or on the gel carrier to form a composite marker.

In at least one aspect, a method of marking a target site in a mammalian subject may be summarized as comprising: administering parenterally to the target site in the mammalian subject a composite marker comprising: a plurality of ultrasound reflective elements, each ultrasound reflective element respectively comprising a body having at least one cavity and at least one fluid in the at least one cavity to provide reflectivity of ultrasound imaging signals; at least one contrast material detectable via a detection modality different than ultrasound imaging, wherein the at least one contrast material is not included in an outer layer of each ultrasound reflective element; and a gel carrier, wherein the ultrasound reflective element and the at least one contrast material are carried in or on the gel carrier. The method also comprises detecting the target site and the composite gel marker with ultrasound imaging or a detection modality capable of detecting the at least one contrast material.

In at least one aspect, a method of marking a target site in a mammalian subject may be summarized as comprising: administering parenterally to the mammalian subject a composite marker, comprising: an activated and/or hydrolyzed fluorescent dye; at least one contrast material detectable by a detection modality different than detection of fluorescence; and a gel carrier, wherein the activated and/or hydrolyzed fluorescent dye and the at least one contrast material are carried in or on the gel carrier. The method also comprises detecting the target site and the composite gel marker with a detection modality that detects fluorescence or a detection modality different than detection of fluorescence and capable of detecting the at least one contrast material.

Additional aspects, advantages and features of the various embodiments and implementations of the invention(s) are set forth in this specification, and in part will become apparent to those skilled in the art on examination of the following, or may be learned by practice of the invention(s). The various embodiments and implementations of invention(s) disclosed in this application is not limited to any particular set of or combination of aspects, advantages and features. It is contemplated that various combinations of the stated aspects, advantages and features make up the various embodiments and implementations of the invention(s) disclosed in this application.

BRIEF DESCRIPTION OF THE DRAWINGS

The drawings are intended to illustrate certain exemplary embodiments and are not limiting. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION OF THE VARIOUS EMBODIMENTS

Figure 1A:
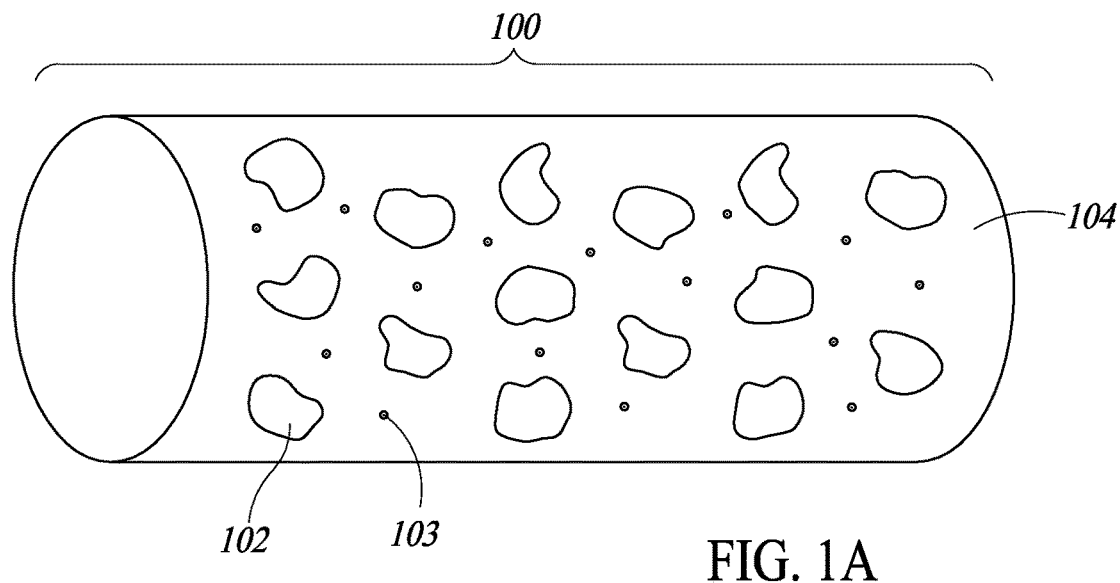
FIG. 1A is an isomeric view of a composite marker according to at least one embodiment, showing the composite marker comprising a plurality of ultrasound reflective elements, at least one contrast material, and a gel carrier, with the ultrasound reflective elements and the contrast material dispersed in the gel carrier.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems including client and server computing systems, and/or communication networks have not been shown or described in detail to avoid unnecessarily obscuring descriptions of the embodiments.

Unless the context requires otherwise, throughout the specification and claims which follow, the word "comprise" and variations thereof, such as "comprises" and "comprising" are to be construed in an open-ended, inclusive sense, e.g., as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

The ability to identify, locate, and mark features within the body of a patient has many useful indications. Identifying a specific area within a patient's body with a marker that may be detected at a later time may be useful for a variety of purposes including monitoring that marked area over time, locating a tumor or other type of tissue lesion or abnormality for subsequent study, and performing treatment or surgical procedure such as ablation, adjuvant therapy, or surgical removal. In certain clinical settings, difficulties may arise where a tissue lesion of interest is most efficiently detected and marked using a first detection modality, but surgical removal of the tissue lesion is best accomplished using a second detection modality. In such cases, a marker embodiment that persists in the tissue and is stable in position for a period time after deployment and that can be detected by at least two distinct detecting modalities may be useful. Some contrast materials, such as fluorescent dye markers (e.g., indocyanine green), although have been used widely in biomedical diagnosis and imaging, still suffer from major limitations for its utilization as a tissue marker in vivo. For instance, in the case of indocyanine green, the limitations are due to its fast clearance, concentration-dependent aggregation, rapid protein binding, and bleaching effect due to various physicochemical attributes. In such cases, a marker embodiment that can encapsulate the contrast material and "lock" it in its activated form may be useful.

The structures, articles and methods described herein provide useful solutions to identify, locate, and mark features within the body of a patient for various purposes. Provided here are new composite tissue markers that employ a gel carrier to carry two or more contrast materials, each detectable by a detection modality different than one another.

A composite marker may comprise a plurality of ultrasound reflective elements, at least one contrast material detectable via a detection modality different than ultrasound imaging, and a gel carrier. Each ultrasound reflective element respectively comprises a body having at least one cavity and at least one fluid in the at least one cavity to provide reflectivity of ultrasound imaging signals. In the case where the ultrasound reflective element has an outer layer (i.e., a layer formed on an outer surface of the ultrasound reflective element, e.g., an outer silica layer), the at least one contrast material is not included in the outer layer of each ultrasound reflective element. The ultrasound reflective element and the at least one contrast material are carried in or on the gel carrier.

FIG. 1A shows an exemplary embodiment of a composite marker 100 that can be used to mark a target site in a mammalian subject. In at least one embodiment, the composite marker 100 comprises a plurality of ultrasound reflective elements 102 (only one called out) and at least one contrast material 103 carried in or on the gel carrier 104. The gel carrier 104 binds the plurality of ultrasound reflective elements 102 and contrast material 103 together.

Ultrasound Reflective Element

The ultrasound reflective element 102 has the structural characteristics to provide reflectivity of ultrasound signals. For instance, each ultrasound reflective element can comprise a body having at least one cavity and at least one fluid in the at least one cavity. The ultrasound reflective element may have irregular surface, for example having a rough outer surface to cause scattering or dispersion of ultrasound energy.

The ultrasound reflective element may take a wide variety of forms. In some embodiments, each ultrasound reflective element is formed of a shell having an outer wall that forms a cavity or a porous particle having more than one cavities.

Figure 1B:
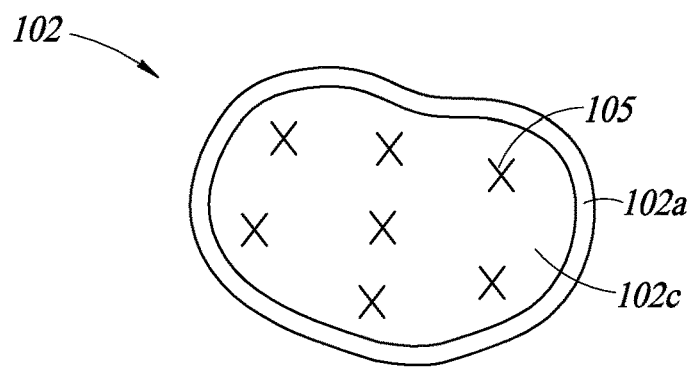
FIG. 1B is an end elevational view of an ultrasound reflective element according to at least one embodiment, comprising a body having at least one cavity and at least one fluid in the at least one cavity to provide reflectivity of ultrasound imaging signals, the body being a shell having an outer wall that forms the cavity.

In at least one embodiment, the ultrasound reflective element comprises a shell having an outer wall that forms a cavity. The shell may be a multi-layer hollow shell, for example a shell with an inner layer and an outer layer. FIG. 1B shows an exemplary embodiment of an ultrasound reflective element 102 comprising a body 102a having at least one cavity 102c and at least one fluid 105 in the at least one cavity 102c to provide reflectivity of ultrasound signals. The body 102a is a shell having an outer wall that forms the cavity.

Figure 1C:
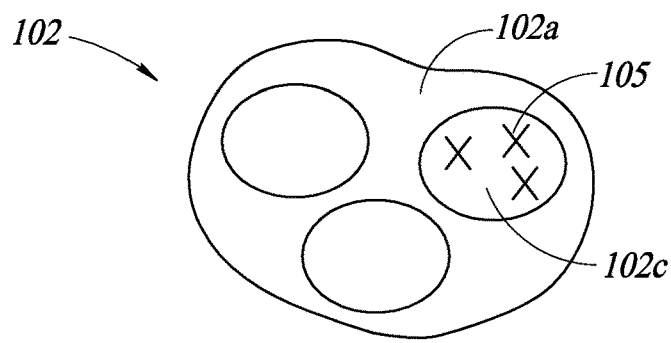
FIG. 1C is an end elevational view of an ultrasound reflective element according to at least one embodiment, comprising a body having at least one cavity and at least one fluid in the at least one cavity to provide reflectivity of ultrasound imaging signals, the body being a porous particle having more than one cavities.
Figure 2A:
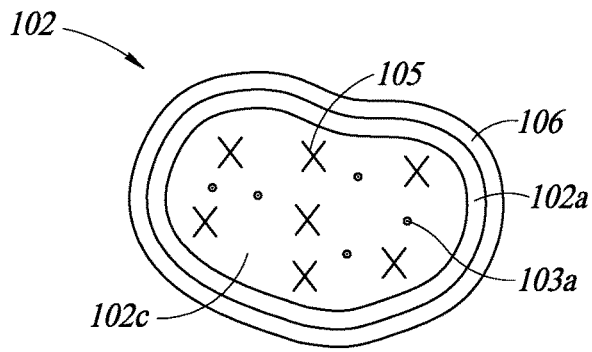
FIG. 2A is an end elevational view of an ultrasound reflective element embodiment of FIG. 1B, with an embodiment of a contrast material inside the cavity of the ultrasound reflective element, and with an optional hydrophobic coating on the ultrasound reflective element.
Figure 2B:
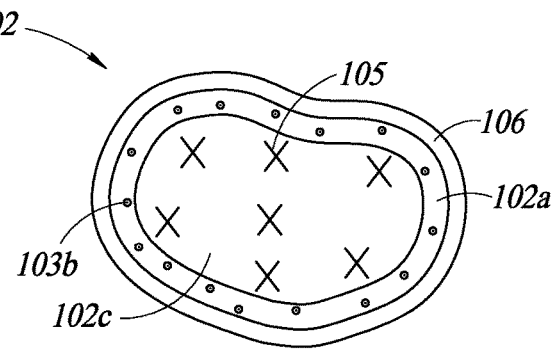
FIG. 2B is an end elevational view of an ultrasound reflective element embodiment of FIG. 1B, with an embodiment of a contrast material embedded in the ultrasound reflective element, and with an optional hydrophobic coating on the ultrasound reflective element.
Figure 2C:
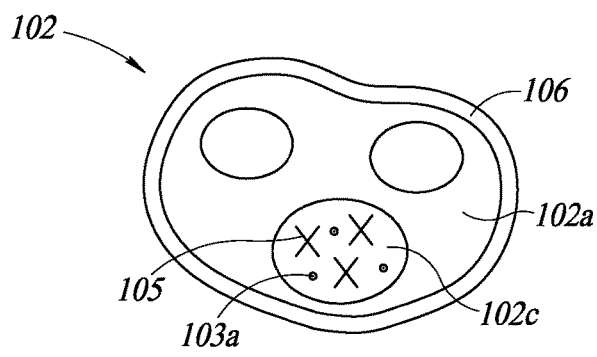
FIG. 2C is an end elevational view of an ultrasound reflective element embodiment of FIG. 1C, with an embodiment of a contrast material inside the cavity of the ultrasound reflective element, and with an optional hydrophobic coating on the ultrasound reflective element.
Figure 2D:
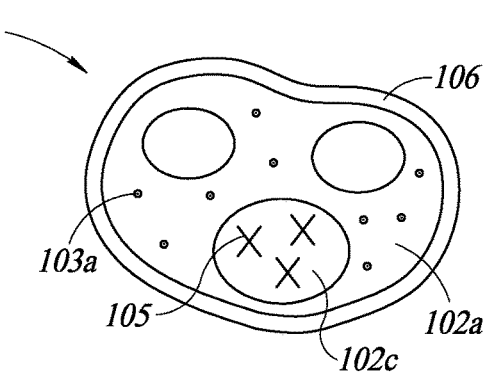
FIG. 2D is an end elevational view of an ultrasound reflective element embodiment of FIG. 1C, with an embodiment of a contrast material embedded in the ultrasound reflective element, and with an optional hydrophobic coating on the ultrasound reflective element.

In at least one embodiment, the ultrasound reflective element is a porous particle having more than one cavities. FIG. 1C shows an exemplary embodiment of an ultrasound reflective element 102 comprising a body 102a having at least one cavity 102c (only one called out) and at least one fluid in the at least one cavity 102c to provide reflectivity of ultrasound signals. The body 102a is a porous particle having more than one cavities.

The body of the ultrasound reflective element may have a spherical shape or a non-spherical shape.

The body of the ultrasound reflective element may be made from a variety of inorganic material that may exist in an amorphous (or glass) state or in a crystalline state or in a mixture of amorphous and crystalline forms. Suitable inorganic materials include, but are not limited to, borate, alumina, carbonate, bicarbonate, silica, silicate, aluminosilicate, titanium dioxide, and phosphate. Any of these inorganic materials may be in the form of a monomeric salt or in a polymeric or condensed form. Any of these inorganic materials may be mixed with one or more other inorganic materials. Exemplary inorganic materials are silica and titanium dioxide.

In some embodiments, the shell or porous particle of the ultrasound reflective element comprises silica or titanium dioxide. In at least one embodiment, the shell or porous particle is silica shell or silica particle.

The techniques to form shells (such as silica shells) suitable for the ultrasound reflective element may be found, for example in: U.S. Pat. Nos. 8,440,229; 9,220,685; 10,328, 160; U.S. patent application Ser. No. 15/706,446; U.S. patent application Ser. No. 15/559,764; and U.S. patent application Ser. No. 15/946,479; all of which are incorporated herein by reference in their entirety. The techniques to form porous particles suitable for the ultrasound reflective element may be found, for example in U.S. Pat. No. 6,254, 852, which is incorporated herein by reference in its entirety.

The at least one fluid 105 in the at least one cavity of the ultrasound reflective element may be entrapped gas or liquid to provide reflectivity of ultrasound signals. The cavity containing the entrapped gas or liquid may act as acoustic wave reflectors because of the acoustic differences between the cavity and the body of the ultrasound reflective element. The entrapped fluid (gas or liquid) may provide a suitable echogenic interface to enhance an ultrasound signal.

Any fluid (gas or liquid) that can be present during the process of preparing the ultrasound reflective element may be suitable. For instance, the entrapped gas may be an elemental gas or a compound gas such as $O_2$, $H_2$, $CO_2$, an inert gas (e.g., $N_2$, helium, argon, or other noble gases). Exemplary entrapped fluids also include a volatile fluid with a boiling point below a bodily temperature (e.g., below 37° C.), such as a fluorocarbon (such as a perfluorocarbon have less than six carbon atoms, e.g., $CF_4$, $C_2F_6$, $C_3F_8$, $C_4F_{10}$, cyclo-$C_4F_8$, $C_5F_{12}$, cyclo-$C_5F_{10}$, cyclo-$C_4F_7$ (1-trifluoromethyl), 2-(trifluoromethyl)-1,1,1,3,3,3-hexafluoro propane, 2-(trifluoromethyl)-1,1,1,3,3,3,4,4,4-nonafluoro butane, perfluorooctane, perfluoro-2-methylpentane, perfluoro-1,3-dimethylcyclohexane, perfluorodecalin, or perfluoromethyldecalin) that is expected to provide useful ultrasound contrast properties. The entrapped fluid may be a mixture of the aforementioned fluids, e.g., air. Additional examples of suitable liquids may be found in U.S. Pat. No. 5,595,723, which is herein incorporated by reference in its entirety.

In an exemplary embodiment, shown in FIG. 1A and FIG. 1B, the cavity 102c of the shell body 102a or the porous particle body 102a contains a fluid 105 (gas or liquid). Suitable fluids in the cavity of the ultrasound reflective element have been discussed above.

In at least one embodiment, the at least one fluid has a vaporization threshold that a liquid-gas transition of the at least one fluid can be triggered by an acoustic energy. For instance, a physical process of vaporization of the liquid can be induced by the pressure waves of ultrasound that cause superheated liquid nanodroplets to form gas bubbles, which can provide ultrasound imaging contrast. A typical candidate for this acoustic vaporization is fluorocarbon fluid. Suitable fluorocarbon fluids have been discussed above. The acoustic vaporization of the fluid may be induced by high intensity focused ultrasound (HIFU) or by low intensity focused ultrasound (LIFU).

In some embodiments, the ultrasound reflective element may comprise one or more layers made from the same or different materials than the body of the ultrasound reflective element.

In some embodiments, each ultrasound reflective element may be porous. For instance, the ultrasound reflective elements may be porous particles as shown, e.g., in FIG. 1C. When the ultrasound reflective element is a shell as shown, e.g., in FIG. 1B, the body of the shell 102a may be porous. Each ultrasound reflective element may optionally comprise a coating, to at least temporarily seal one or more pores thereof, so that the fluid in the at least one cavity of the ultrasound reflective element is entrapped in the cavities or pores of the ultrasound reflective element. FIGS. 2A-2D show exemplary embodiments of an ultrasound reflective element 102 with an optional coating 106 (e.g., a hydrophobic coating) on the ultrasound reflective element.

The coating 106 may be a natural material such as a protein (e.g., collagen, gelatin, fibrin, fibronectin, or albumin), or a polysaccharide (e.g., cellulose or methyl cellulose, hyaluronic acid, chitin, chitosan, or calcium alginate). The coating may be a synthetic polymer such as polyvinyl alcohol (PVA), polyglycolic acid (PGA), polylactic acid (PLA), poly(glycolic-co-lactic acid) (PLGA), polycaprolactone (PCL), polymethacrylate (PMA), polymethylmethacrylate (PMMA), polyethylene oxide (PEO), polyamine, polyoxaamide, polyoxaester, polyethylene glycol (PEG), polypropylene (PP), polytetrafluoroethylene (PTFE), polyester, polyetheretherketone (PEEK), or a copolymer of any of the aforementioned polymers. The coating may be a mixture of any two or more aforementioned materials.

The coating may optionally be a hydrophobic coating. For instance, the coating may be a mono-, di-, tri-, or tetra-alkoxysilane, including but not limited to, propyltrimethoxysilane, hexyltrimethoxysilane, heptyltrimethoxysilane, octyltrimethoxysilane, nonyltrimethoxysilane, decyltrimethoxysilane, dodecyltrimethoxysilane, tridecyltrimethoxysilane, tetradecyltrimethoxysilane, pentadecyltrimethoxysilane, hexadecyltrimethoxysilane, heptadecyltrimethoxysilane, octadecyltrimethoxysilane, phenyltrimethoxysilane, propyltriethoxysilane, hexyltriethoxysilane, heptyltriethoxysilane, octyltriethoxysilane, nonyltriethoxysilane, decyltriethoxysilane, dodecyltriethoxysilane, tridecyltriethoxysilane, tetradecyltriethoxysilane, pentadecyltriethoxysilane, hexadecyltriethoxysilane, heptadecyltriethoxysilane, octadecyltriethoxysilane, phenyltriethoxysilane, methoxy (triethyleneoxy) propyltrimethoxysilane, 3-(methacryloyloxy) propyltrimethoxysilane, m, p-ethylphenethyltrimethoxysilane, 2-[methoxy (polyethyleneoxy) propyl]-trimethoxysilane, 3-aminopropyltrimethoxysilane, 3-mercaptopropyltrimethoxysilane, 3-isocyanatopropyltriethoxysilane, 3-isocyanatopropyltrimethoxysilane, and glycidoxypropyltrimethoxysilane. In at least one embodiment, the hydrophobic coating takes the form of a hydrophobic polymer, for instance a hydrophobic polymer comprising octyltriethoxysilane.

Methods for coating particles are described by Lachman et al., The Theory and Practice of Industrial Pharmacy (Lea & Febiger, 1986), which is incorporated herein by reference in its entirety. The techniques for coating particles less than about 100 microns typically include air suspension, coacervation-phase separation, multi-orifice centrifugal, and solvent evaporation.

The ultrasound reflective element can have a distinct signal in ultrasound, such as in Doppler ultrasound imaging. In some embodiments, the composite marker comprising such ultrasound reflective elements, when administered to a target site in a mammalian subject, can provide significantly less marker migration relative to traditional wire localization. In at least one embodiment, the ultrasound reflective elements may be identified intraoperatively with color Doppler ultrasound imaging and B-mode ultrasound imaging in an intraoperative setting.

Under B-mode ultrasound imaging, the ultrasound reflective element in some composite gel marker embodiments discussed herein may appear similar to other commercially available ultrasound markers. In some cases, under Doppler mode, the ultrasound reflective elements in some composite gel marker embodiments discussed herein may generate a robust, highly-colored signal. Therefore, they may emit a colorful signal under Doppler ultrasound, allowing for rapid identification with any standard ultrasound machine.

The ultrasound reflective element may have a size ranging from about 50 nm to about 20 microns. For instance, the ultrasound reflective element may range from about 50 nm to about 500 nm, from 50 nm to about 350 nm, from about 100 nm to about 2.2 microns, or from about 200 nm to about 2 microns. The ultrasound reflective element may have a larger size that may promote stronger reflective ultrasound signals, ranging from about 1 micron to about 20 microns, e.g., from about 1 micron to about 5 microns, or from about 1.8 microns to about 2.2 microns.

Other Contrast Materials

The composite marker 100 also comprises at least one contrast material 103. Suitable contrast materials may include a wide variety of materials that can produce a return signal distinct from that of the surrounding tissue and can be detected via a variety of corresponding detection modalities different than ultrasound imaging and including, such as X-ray imaging, visual observation, fluoroscopy, MRI, nuclear-based imaging, and the like.

The at least one contrast material 103 may include two or more different contrast materials, each detectable by a respective detection modality that is different from one another and different from ultrasound imaging.

The at least one contrast material may include, for instance, a radiopaque material, detectable via X-ray imaging (e.g., computed tomography, fluoroscopy). Suitable radiopaque materials include a radiopaque metal, such as stainless steel, platinum, gold, iridium, titanium, tantalum, tungsten, silver, rhodium, nickel, bismuth, and barium. Suitable radiopaque materials also include an alloy of two or more of the radiopaque metals, an oxide of the radiopaque metal, a sulfate of the radiopaque metal, and a carbonate of the radiopaque metals. A combination of any two or more aforementioned radiopaque materials can be used as the contrast material.

The at least one contrast material may include, for instance, a visually detectable materials such as a dye or a pigment. Exemplary visually detectable materials are a pigment, a visible dye, a fluorescent dye, a near-infrared dye, and a UV dye. In some embodiments, the at least one contrast material includes a cyanine dye selected from the group consisting of a carbocyanine, an oxacarbocyanine, a thiacarbocyanine, and a merocyanine. In some embodiments, the at least one contrast material includes at least one of: methylene blue, indigo dye, or indocyanine green. In at least one embodiment, the at least one contrast material includes indocyanine green.

The at least one contrast material may include, for instance, a material detectable via magnetic resonance imaging (MRI), such as a paramagnetic, superparamagnetic, ferrimagnetic or ferromagnetic compound, or a compound containing other non-zero spin nuclei than hydrogen. Exemplary MRI-detectable materials are a manganese or manganese-based compound; a gadolinium or gadolinium-based compound (e.g., gadolinium DTPA); and ferrous gluconate, ferrous sulfate, iron oxide, or iron platinum.

The at least one contrast material may include, for instance, a radioactive material, detectable via nuclear-based imaging (e.g., scintigraphy, positron emission tomography, or single-photon emission computed tomography). Exemplary radioactive material are radioiodinated compounds, $^{111}$Indium labelled materials, $^{99m}$Tc labelled compounds (e.g., $^{99m}$TcDTPA, $^{99m}$TcHIDA and $^{99m}$Tc labelled polyphosphonates), and $^{51}$Cr labelled compounds (e.g., $^{51}$CrEDTA).

The at least one contrast material 103 may be carried in or on the gel carrier 104 in a dispersion therein, optionally in a colloidal dispersion. In some embodiments, the plurality of ultrasound reflective elements 102 and the at least one contrast material 103 are carried in or on the gel carrier 104 in a dispersion therein, optionally in a colloidal dispersion. FIG. 1A shows an exemplary embodiment of a composite marker 100 where the plurality of ultrasound reflective elements 102 and the at least one contrast material 103 are carried in or on the gel carrier 104 in a dispersion therein, optionally in a colloidal dispersion.

Figure 3:
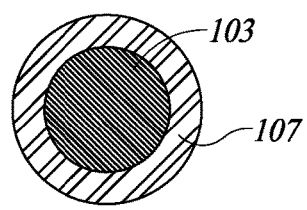
FIG. 3 is an enlarged view of a contrast material embodiment in FIG. 1A, with the contrast material having an optional coating or encapsulation of a shell.

When the at least one contrast material is dispersed in the gel carrier, to prevent the at least one contrast material from effusing out of the gel carrier, the at least one contrast material may further comprise a coating or encapsulation of a shell. FIG. 3 shows an exemplary embodiment of a contrast material, with an optional coating or encapsulation of a shell 107 on the outer surface of the contrast material 103. This optional coating or encapsulation of a shell can be formed from a variety of inorganic materials including but not limited to borate, alumina, carbonate, bicarbonate, silica, silicate, aluminosilicate, titanium dioxide, and phosphate. Any of these inorganic materials may be in the form of a monomeric salt or in a polymeric or condensed form. Any of these inorganic materials may be mixed with one or more other inorganic materials. Exemplary inorganic materials are silica and titanium dioxide. In at least one embodiment, the at least one contrast material further comprises a silica or titanium dioxide coating or encapsulation of a silica or titanium dioxide shell.

The at least one contrast material 103 may be carried by the ultrasound reflective elements 102. In at least one embodiment, at least one contrast material may be inside the cavity of the ultrasound reflective element. For instance, in FIG. 2A and FIG. 2C, a contrast material 103a, together with a fluid 105, is inside the cavity of the ultrasound reflective element 102c. In at least one embodiment, at least one contrast material may be embedded in the body of the ultrasound reflective element. For instance, in FIG. 2B and FIG. 2D, a contrast material 103b is carried in the body of the ultrasound reflective element 102a. When the ultrasound reflective element comprises one or more layers, at least one contrast material is not in these layers of the ultrasound reflective element.

In at least one embodiment, the at least one contrast material can be entrapped in the ultrasound reflective element (e.g., silica shell or silica particle) together with a fluid (e.g., a perfluorocarbon fluid) using single emulsion method.

Gel Carrier

The composite marker 100 also comprises a gel carrier 104, which may comprise a natural gelatinous material, a synthetic polymer, or a combination thereof. Suitable natural gelatinous materials include a protein (e.g., collagen, gelatin, fibrin, fibronectin, and albumin), and a polysaccharide (e.g., cellulose or methyl cellulose, hyaluronic acid, chitin, chitosan, and calcium alginate). Suitable synthetic polymers include polyvinyl alcohol (PVA), polyglycolic acid (PGA), polylactic acid (PLA), poly(glycolic-co-lactic acid) (PLGA), polycaprolactone (PCL), polymethacrylate (PMA), polymethylmethacrylate (PMMA), polyethylene oxide (PEO), polyamine, polyoxaamide, polyoxaester, polyethylene glycol (PEG), polypropylene (PP), polytetrafluoroethylene (PTFE), polyester, polyetheretherketone (PEEK), and a copolymer of any of the aforementioned polymers. A mixture of any two or more materials selected from any aforementioned natural gelatinous materials and synthetic polymers can be used as the gel carrier. In at least one embodiment, the gel carrier comprises a natural collagen or gelatin. In at least one embodiment, the gel carrier comprises a synthetic PVA or PEG.

The gel carrier 104 may degrade in vivo in the tissues of a host mammalian subject within of a short period of time (a few weeks to a few months) or may persist in the tissues of a host mammalian subject over a long period of time (e.g., 60 years or longer). The gel carrier may be at least partially crosslinked to decrease the rate of degradation and to persist in the tissues of the host mammalian subject for a prolonged period of time, for instance, over a period of hours, days, a week or weeks, a month or months, or even for a year or years. When degradable, the rate of degradation of the composite marker in the tissues of a host mammalian subject may be controlled by the degree of crosslinking of the gel carrier. The biological degradation takes place at a slower rate as the degree of crosslinking increases.

In some embodiments, the gel carrier may have at least partially degraded over a period of time, exposing at least some of the contrast materials carried in or on the gel carrier to the bodily tissues. The exposed contrast materials may degrade in vivo in the tissues of a host mammalian subject within of a short period of time (a few weeks to a few months) or may persist in the tissues of a host mammalian subject over a long period of time (e.g., 60 years or longer).

In some embodiments, the degree of crosslinking of the gel carrier is pre-determined by the rate of degradation of the composite marker in the tissues of a host mammalian subject. In at least one embodiment, the rate of degradation is such that the composite marker persists in the tissues of the host mammalian subject for a period of at least three weeks, at least four weeks, at least three months, at least six months, or at least nine months.

The crosslinking or partial crosslinking of the gel carrier may be achieved by a physical process or a chemical modification (with or without using a crosslinking agent). Suitable physical processes are those known to one skilled in the art, including but not limited to, drying (e.g., freeze-drying, critical point drying, or air drying), thermo-dehydration, and radiation (e.g., UV radiation or γ-ray radiation). Suitable chemical modifications are those known to one skilled in the art, including but not limited to, liquid phase crosslinking (e.g., the gel is immersed in a solution of a crosslinking agent to react, and the unreacted crosslinking agent is washed off), vapor phase crosslinking (e.g., the crosslinking reaction of the gel is performed under the vapor of the crosslinking agent, and the unreacted crosslinking agent is flushed off with an air flow), and supercritical fluid crosslinking (e.g., the gel is contacted with a supercritical fluid containing a crosslinking agent to react).

In at least one embodiment, the gel carrier is rendered at least partially crosslinked by freezing and/or thawing.

In at least one embodiment, the gel carrier is rendered at least partially crosslinked by using a crosslinking agent. Suitable crosslinking agents are those known to one skilled in the art for use in crosslinking of polymers, including but not limited to, an aldehyde (e.g., formaldehyde), glutaraldehyde, glyceraldehyde, dialdehyde, starch, epoxide, dimethyl adipimidate, glucosepane, carbodiimide, pentosidine, isocyanate or polyisocyanate, metallic crosslinker, ionic crosslinker, acrylic compound, alginate, sulfhydryl, genipin, and a combination thereof.

The degree of crosslinking of the gel carrier may be tailored by altering the crosslinking processing duration (for a physical process), the crosslinking reaction time (for a chemical process), the concentration of the crosslinking agent (for a chemical process), the operating temperature or pressure, and other process parameters or reaction conditions.

The gel carrier may be prepared from a gel or gel forming material. For instance, a dry gel or gel forming material may be mixed with distilled water in a variety of concentrations to tailor the resulting properties to a particular indication or use, for example, in a concentration of about 1 wt % 1 g gel or gel forming material per 100 ml distilled water) to about 50 wt %, such as about 1 wt % to about 10 wt %, about 4 wt % to about 10 wt %, or about 4 wt % to about 6 wt %.

A composite marker may comprise an activated and/or hydrolyzed fluorescent dye; at least one contrast material detectable by a detection modality different than detection of fluorescence; and a gel carrier. The activated and/or hydrolyzed fluorescent dye and the at least one contrast material are carried in or on the gel carrier.

Figure 4A:
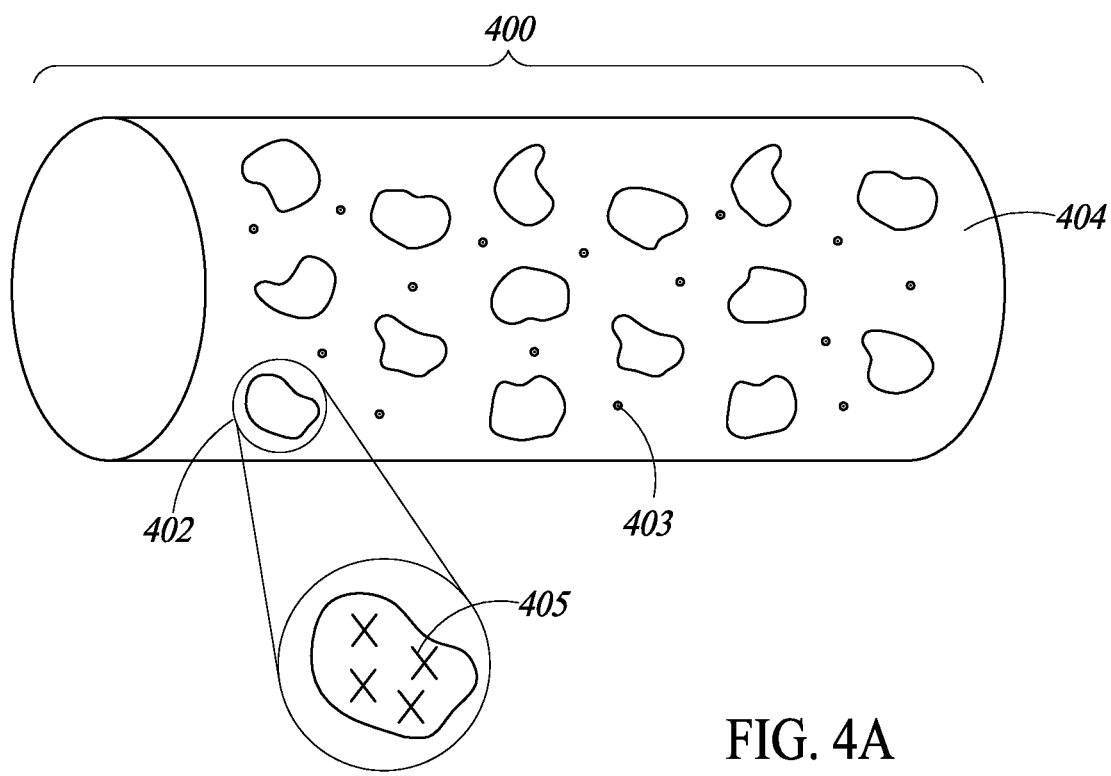
FIG. 4A is an isomeric view of a composite marker according to at least one embodiment, showing the composite marker comprising an activated and/or hydrolyzed fluorescent dye, at least one contrast material, and a gel carrier, with the contrast material and the activated and/or hydrolyzed fluorescent dye dispersed in the gel carrier. An enlarged view shows that one contrast material is optionally an ultrasound reflective element containing a fluid in the cavity of the ultrasound reflective element.

FIG. 4A shows an exemplary embodiment of a composite marker 400 that can be used to mark a target site in a mammalian subject. In at least one embodiment, the composite marker 400 comprises an activated and/or hydrolyzed fluorescent dye 403 and at least one contrast material 402 carried in or on the gel carrier 404. The gel carrier 404 binds the activated and/or hydrolyzed fluorescent dye 403 and the at least one contrast material 402 together.

Fluorescent Dye

The activated and/or hydrolyzed fluorescent dye 403 may be formed by activating and/or hydrolyzing a fluorescent dye when exposing the fluorescent dye to the gel carrier when forming the composite marker. The phrase "activated and/or hydrolyzed fluorescent dye" refers to a form of a fluorescent dye molecule that is formed when exposing the fluorescent dye material to the gel carrier to prepare the composite marker, during which process the fluorescent dye molecule is activated and/or hydrolyzed so that it can emit fluorescence. By forming a composite marker using a gel carrier, the fluorescent dye molecule is "locked" (or at least prolonged) in its activated and/or hydrolyzed form so that the photobleaching effect may be minimized. Taking ICG as an example, in aqueous solution, ICG has the maximum absorption at 780 nm and a relatively low quantum yield for fluorescence. Nevertheless, free form of ICG can be rapidly cleared from the blood stream and photobleaching. When incorporating ICG into the gel carrier to form the composite marker, ICG is exposed to the water component in the gel carrier to be activated and/or hydrolyzed, which may provide a same or similar absorption signature as ICG in solution. Moreover, incorporating the activated and/or hydrolyzed ICG in the composite marker may decrease the bleaching effect of the ICG dye and increase the effective length of time in which the ICG dye can be detected and monitored.

Suitable fluorescent dyes include, but are not limited to, a cyanine dye, such as a carbocyanine, an oxacarbocyanine, a thiacarbocyanine, and a merocyanine. An exemplary cyanine dye is indocyanine green.

The composite marker 400 also comprises at least one contrast material 402. The at least one contrast material 402 may include two or more different contrast materials, each detectable by a respective detection modality that is different from one another and different than detection of fluorescence.

In some embodiments, the at least one contrast material 402 comprises a plurality of ultrasound reflective elements 102 each respectively comprising a body having at least one cavity and at least one fluid in the at least one cavity to provide reflectivity of ultrasound imaging signals. In some embodiments, the at least one contrast material 402 comprises a plurality of ultrasound reflective elements 102 each respectively comprising a body having at least one cavity and at least one fluid 405 in the at least one cavity to provide reflectivity of ultrasound imaging signals.

In these embodiments, all above descriptions and embodiments relating to the ultrasound reflective element 102, including the variety of forms that the ultrasound reflective element 102 takes, the shape and materials of the body of the ultrasound reflective element 102a, the techniques for form the ultrasound reflective element, the fluid 105 entrapped in the cavity of the ultrasound reflective element, the coating 106 on the ultrasound reflective element, the size of the ultrasound reflective element, and the exemplary embodiments shown in FIGS. 1B-1C and FIGS. 2A-2D, are all applicable to the embodiment(s) or implementation(s) relating to the at least one contrast material 402 in the composite marker 400.

In some embodiments, the at least one contrast material 402 comprises a plurality of ultrasound reflective elements 102, each being formed of a shell 102a having an outer wall that forms a cavity 102c or a porous particle 102a having more than one cavities 102c (as shown in FIGS. 1B and 1C). In some embodiments, the shell or porous particle comprises silica or titanium dioxide. In at least one embodiment, the shell or porous particle is silica shell or silica particle.

In some embodiments, the at least one contrast material 402 comprises a plurality of ultrasound reflective elements 102, each respectively comprising a body having at least one cavity containing entrapped fluid (gas or liquid) 405 to provide reflectivity of ultrasound imaging signals. In at least one embodiment, the at least one fluid has a vaporization threshold that a liquid-gas transition of the at least one fluid can be triggered by an acoustic energy. The acoustic vaporization of the fluid may be induced by high intensity focused ultrasound (HIFU) or by low intensity focused ultrasound (LIFU).

In some embodiments, the at least one contrast material 402 comprises a radiopaque material, detectable via X-ray imaging (e.g., computed tomography, fluoroscopy). Suitable radiopaque materials have been discussed above relating to the at least one contrast material 103.

In some embodiments, the at least one contrast material 402 comprises a material visually detectable materials in a detection modality other than detection of fluorescence, such as a dye or a pigment, that is not a fluorescent dye. Exemplary visually detectable materials are a pigment, a visible dye, and a UV dye. In at least one embodiment, the at least one contrast material includes at least one of: methylene blue and indigo dye.

In some embodiments, the at least one contrast material 402 comprises a material detectable via magnetic resonance imaging (MRI). Suitable MRI-detectable materials have been discussed above relating to the at least one contrast material 103.

In some embodiments, the at least one contrast material 402 comprises a radioactive material, detectable via nuclear-based imaging (e.g., scintigraphy, positron emission tomography, or single-photon emission computed tomography). Suitable radioactive materials have been discussed above relating to the at least one contrast material 103.

The activated and/or hydrolyzed fluorescent dye 403 may be carried in or on the gel carrier 404 in a dispersion therein, optionally in a colloidal dispersion. In some embodiments, the at least one contrast material 402 and the activated and/or hydrolyzed fluorescent dye 403 are carried in or on the gel carrier 404 in a dispersion therein, optionally in a colloidal dispersion. FIG. 4A shows an exemplary embodiment of a composite marker 400 where the at least one contrast material 402 and the activated and/or hydrolyzed fluorescent dye 403 are carried in or on the gel carrier 404 in a dispersion therein, optionally in a colloidal dispersion.

When the fluorescent dye is dispersed in the gel carrier, to prevent the activated and/or hydrolyzed fluorescent dye from effusing out of the gel carrier, the activated and/or hydrolyzed fluorescent dye may further comprise a coating or encapsulation of a shell. This coating or encapsulation of a shell can be formed from a variety of inorganic material including but not limited to borate, alumina, carbonate, bicarbonate, silica, silicate, aluminosilicate, titanium dioxide, and phosphate. Any of these inorganic materials may be in the form of a monomeric salt or in a polymeric or condensed form. Any of these inorganic materials may be mixed with one or more other inorganic materials. Exemplary inorganic materials are silica and titanium dioxide. In at least one embodiment, the activated and/or hydrolyzed fluorescent dye further comprises a silica or titanium dioxide coating or encapsulation of a silica or titanium dioxide shell.

When the at least one contrast material is dispersed in the gel carrier, the at least one contrast material may also further comprise a coating or encapsulation of a shell, to prevent the at least one contrast material from effusing out of the gel carrier.

Figure 4B:
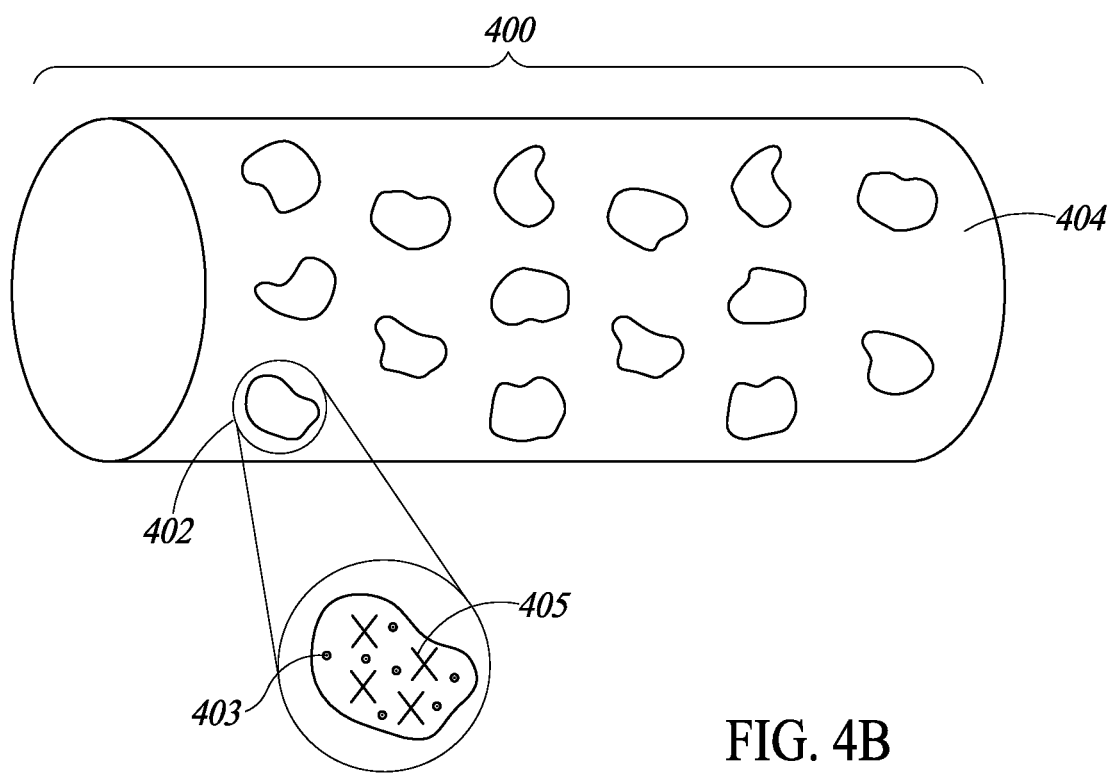
FIG. 4B is an isomeric view of a composite marker according to at least one embodiment, showing the composite marker comprising an activated and/or hydrolyzed fluorescent dye, at least one contrast material, and a gel carrier, with the contrast material dispersed in the gel carrier. An enlarged view shows that one contrast material is optionally an ultrasound reflective element containing a fluid in the cavity of the ultrasound reflective element, and the activated and/or hydrolyzed fluorescent dye is embedded in the contrast material.

In some embodiments, the activated and/or hydrolyzed fluorescent dye may be carried on or embedded in the at least one contrast material 402. For instance, in FIG. 4B, the activated and/or hydrolyzed fluorescent dye 403 is carried on or embedded in the at least one contrast material 402.

In at least one embodiment, the at least one contrast material 402 comprises a plurality of ultrasound reflective elements 102, each respectively comprising a body having at least one cavity containing entrapped fluid (gas or liquid) 405 to provide reflectivity of ultrasound imaging signals; and the activated and/or hydrolyzed fluorescent dye may be carried on or embedded in the at least one contrast material 402. For instance, in FIG. 4B, the activated and/or hydrolyzed fluorescent dye 403, together with the entrapped fluid 405, is carried on or embedded in the ultrasound reflective element 402 (or 102). In this embodiment, the activated and/or hydrolyzed fluorescent dye may be inside the cavity of the ultrasound reflective element and/or embedded in the body of the ultrasound reflective element, similar to the exemplary embodiments illustrated in FIGS. 2A-2D.

In at least one embodiment, the activated and/or hydrolyzed fluorescent dye, such as ICG, can be entrapped in the ultrasound reflective element (e.g., silica shell or silica particle) together with a fluid (e.g., a perfluorocarbon fluid) using single emulsion method.

The composite marker 400 also comprises a gel carrier 404, which may comprise a natural gelatinous material, a synthetic polymer, or a combination thereof.

All above descriptions and embodiments discussed relating to the gel carrier 104, including suitable materials for the gel carrier, crosslinking of the gel carrier, the form and size of the gel carrier, and the preparation of the gel carrier, are all applicable to the embodiment(s) or implementation(s) relating to the gel carrier 404 in the composite marker 400.

In at least some implementations, the composite marker may be expandable, for example when implanted into bodily tissue. The composite marker may be able to hydrate rapidly, achieving full hydration when disposed within an aqueous environment within 24 hours in some cases.

In some embodiments, the composite marker may, in an unexpanded state, have a length of about 2 mm to about 40 mm and a transverse dimension of about 0.5 mm to about 2 mm. The composite marker may have a ratio of size expansion from a dried unexpanded state to a water saturated expanded state of about 1:1.5 to about 1:10. The composite marker may have a ratio of size expansion from a dried unexpanded state to a water saturated expanded state of about 1:2 to about 1:3.

The composite marker may take a variety of forms, depending on the mold used when molding the composite marker.

In some embodiments, the composite marker may have an axial length of about 1 cm to about 10 cm, for instance, from about 2 cm to about 8 cm. In an exemplary embodiment, an outer transverse dimension of the composite marker molded in a 2 mm silicone tube may be about 0.025 to about 0.031 inches, about 0.026 to about 0.030 inches, or about 0.027 to about 0.028 inches. It may have a dry weight of about 7 to about 7.8 mg and in some cases, an axial length of about 22 mm to about 24 mm. Upon soaking the composite marker in water, it may expand to an outer transverse dimension of about 1.5 mm with an axial length of about 23 mm to about 25 mm in some cases. In an exemplary embodiment, an outer transverse dimension of the composite marker molded in 2.4 mm silicone tubes may be about 0.026 to about 0.034 inches, about 0.029 to about 0.033 inches, or about 0.031 to about 0.032 inches after being freeze dried and subsequently compressed. It may have a dry weight of about 6.2 mg to about 8 mg.

In some embodiments, the composite marker may have a pellet shape, i.e., having a relatively shorter axial length. For instance, the composite marker may have a transverse dimension of about 1 mm to about 3 mm and an axial length of about 2 mm to about 10 mm.

A kit for forming a composite marker may comprise a plurality of ultrasound reflective elements; at least one contrast material detectable via a detection modality different than ultrasound imaging; and a gel or gel forming material. Each ultrasound reflective element respectively comprises a body having at least one cavity and at least one fluid in the at least one cavity to provide reflectivity of ultrasound imaging signals. The at least one contrast material is not included in an outer layer of each ultrasound reflective element. When being mixed with the plurality of ultrasound reflective elements and the at least one contrast material, the gel or gel forming material results in a gel carrier which carries the plurality of ultrasound reflective elements and the at least one contrast material in or on the gel carrier to form a composite marker. The kit may further comprise a crosslinking agent.

All above descriptions and embodiments relating to the composite marker 100, including descriptions and embodiments relating to the ultrasound reflective element 102, the at least one contrast material 103, and the gel carrier 104, are all applicable to the embodiment(s) or implementation(s) of a kit for forming a composite marker.

A kit for forming a composite marker may comprise a fluorescent dye; at least one contrast material detectable by a detection modality different than detection of fluorescence; and a gel or gel forming material. When being mixed with the at least one contrast material and the fluorescent dye, the gel or gel forming material results in a gel carrier which carries the at least one contrast material and the fluorescent dye in or on the gel carrier to form a composite marker. The kit may further comprise a crosslinking agent.

All above descriptions and embodiments discussed in the above aspect relating to the composite marker 400, including descriptions and embodiments relating to the fluorescent dye 403, the at least one contrast material 402, and the gel carrier 404, are all applicable to the embodiment(s) or implementation(s) of a kit for forming a composite marker.

A method for forming a composite marker may comprise: mixing: 1) a plurality of ultrasound reflective elements, each ultrasound reflective element respectively comprising a body having at least one cavity and at least one fluid in the at least one cavity to provide reflectivity of ultrasound imaging signals; 2) at least one contrast material detectable by a detection modality different than ultrasound imaging, wherein the at least one imaging material is not included in an outer layer of each ultrasound reflective element; and 3) a gel or gel forming material, to result in a gel carrier carrying the plurality of ultrasound reflective elements and the at least one contrast material in or on the gel carrier to form a composite marker.

All above descriptions and embodiments discussed in the above aspect relating to the composite marker 100, including descriptions and embodiments relating to the ultrasound reflective element 102, the at least one contrast material 103, and the gel carrier 104, are all applicable to a method for forming a composite marker 100.

In some embodiments, the plurality of ultrasound reflective elements are mixed with the at least one contrast material first, so that the contrast material may be carried by the ultrasound reflective elements. In some embodiments, the plurality of ultrasound reflective elements are mixed with the at least one contrast material during the process of preparing the ultrasound reflective elements, so that the contrast material may be carried by the ultrasound reflective elements. Mixing may infuse the at least one contrast material into the cavity of the ultrasound reflective element. Mixing may infuse the at least one contrast material in the body of the ultrasound reflective element.

The plurality of ultrasound reflective elements carrying the at least one contrast material are then mixed with the gel or gel forming material to result in a gel carrier carrying the plurality of ultrasound reflective elements and the at least one contrast material in or on the gel carrier to form a composite marker.

In some embodiments, the at least one contrast material and the gel or gel forming material are mixed together in one step, so that the contrast material may be carried in or on the gel carrier in a dispersion therein, optionally in a colloidal dispersion.

In some embodiments, the plurality of ultrasound reflective elements, the at least one contrast material, and the gel or gel forming material are all mixed together in one step, so that the plurality of ultrasound reflective elements and the contrast material may be carried in or on the gel carrier in a dispersion therein, optionally in a colloidal dispersion.

A method for forming a composite marker may comprise: mixing: 1) a fluorescent dye; 2) at least one contrast material detectable by a detection modality different than detection of fluorescence; and 3) a gel or gel forming material, to result in a gel carrier carrying the fluorescent dye and the at least one contrast material in or on the gel carrier to form a composite marker.

In some embodiments, the mixing further comprises exposing the fluorescent dye to the gel or gel forming material to form an activated and/or hydrolyzed fluorescent dye, carried in or on the gel carrier.

All above descriptions and embodiments discussed in the above aspect relating to the composite marker 400, including descriptions and embodiments relating to the fluorescent dye 403, the at least one contrast material 402, and the gel carrier 404, are all applicable to a method for forming a composite marker 400.

In some embodiments, the fluorescent dye is mixed with the at least one contrast material (e.g., a plurality of ultrasound reflective elements) first, so that the fluorescent dye may be carried by the at least one contrast material (e.g., the plurality of ultrasound reflective elements). In some embodiments, the fluorescent dye is mixed with the at least one contrast material (e.g., a plurality of ultrasound reflective elements) during the process of preparing the at least one contrast material (e.g., the plurality of ultrasound reflective elements), so that the fluorescent dye may be carried by the at least one contrast material (e.g., the plurality of ultrasound reflective elements). Mixing may infuse the fluorescent dye into the cavity of at least one contrast material (e.g., the plurality of ultrasound reflective elements). Mixing may infuse the fluorescent dye in the body of the at least one contrast material (e.g., the plurality of ultrasound reflective elements).

The at least one contrast material (e.g., the plurality of ultrasound reflective elements) carrying the fluorescent dye is then mixed with the gel or gel forming material to result in a gel carrier carrying the fluorescent dye and the at least one contrast material (e.g., the plurality of ultrasound reflective elements) in or on the gel carrier to form a composite marker.

In some embodiments, the fluorescent dye and the gel or gel forming material are mixed together in one step, so that the fluorescent dye may be carried in or on the gel carrier in a dispersion therein, optionally in a colloidal dispersion.

In some embodiments, the fluorescent dye, the at least one contrast material (e.g., the plurality of ultrasound reflective elements), and the gel or gel forming material are all mixed together in one step, so that the fluorescent dye and the contrast material (e.g., the plurality of ultrasound reflective elements) may be carried in or on the gel carrier in a dispersion therein, optionally in a colloidal dispersion.

A method for forming a composite marker may further comprise carrying out a physical process or a chemical modification to the gel carrier to at least partially crosslink the gel carrier.

In some embodiments, the method further comprises drying (e.g., freeze-drying, critical point drying, or air drying), thermo-dehydrating, or radiating (e.g., UV radiating or γ-ray radiating) to at least partially crosslink the gel carrier. In at least one embodiment, the method further comprises freezing and/or thawing to at least partially crosslink the gel carrier.

In some embodiments, the method further comprises adding a crosslinking agent to the gel or gel forming material to at least partially crosslink the gel carrier. Suitable crosslinking agents have been discussed above.

A method for forming a composite marker may further comprise molding/casting the composite marker by a mold based on the shape desired (e.g., a tubular mold). For instance, the composite marker may be molded into an inner cylindrical cavity of a silicone tube; the composite marker may be frozen and/or freeze dried; the composite marker may be pushed out of the inner cylindrical cavity; and the composite marker may be pressed (or compressed) to remove air and reduce the volume and outer profile such that the composite marker will fit in an inner lumen of a cannula of a syringe applicator. The composite marker may also be compressed and de-aired after being freeze-dried while still disposed within an inner lumen of a silicone tube. In some embodiments, the freeze-dried composite markers may be compressed by rolling them between two silicone sheet surfaces to remove air pockets and reduce profile.

In a method for forming a composite marker, the total amounts of all types of contrast materials (including ultrasound reflective elements, fluorescent dye, and other contrast materials) and gel or gel forming material may be used in a ratio ranging from about 0.1 mg/ml (i.e., 0.1 mg contrast material per 1 ml gel or gel forming material) to about 10 mg/ml, for instance, from about 0.1 mg/ml to about 8 mg/ml, or from about 2 mg/ml to about 5 mg/ml.

In an exemplary embodiment for forming a composite marker, a methylene blue or ICG solution/suspension (in ethanol) (about 5%) is mixed with about 2 mg silica shells and about 1 ml chitosan. The mixture is dispensed (e.g., injected) into an inner cylindrical cavity of a tubular mold made from a soft elastic material (e.g., a tubular silicone mold having an inner lumen diameter of about 2.3 mm to about 2.5 mm). The silicon tube is then frozen and subsequently freeze dried with a 20-25% sodium hydroxide solution.

In an exemplary embodiment for forming a composite marker, a methylene blue or ICG solution/suspension (in ethanol) (about 5%) is mixed with about 2 mg silica shells and about 1 ml 5 wt %-10 wt % PVA aqueous solution (99% hydrolyzed; MW 78,000). The mixture is injected into a silicone tube. The tube is then frozen and subsequently freeze dried with a 20-25% sodium hydroxide solution.

The freeze dried composite marker may then be removed from the mold (e.g., silicone tube), and may be sized and configured to fit into a various size syringe applicator device (e.g., standard 14-gauge, or 19- or 20-gauge) with sufficient interference for an accurate and timely deployment.

A method of marking a target site in a mammalian subject may comprise: administering parenterally to the target site in the mammalian subject a composite marker comprising: a plurality of ultrasound reflective elements, each ultrasound reflective element respectively comprising a body having at least one cavity and at least one fluid in the at least one cavity to provide reflectivity of ultrasound imaging signals; at least one contrast material detectable via a detection modality different than ultrasound imaging, wherein the at least one contrast material is not included in an outer layer of each ultrasound reflective element; and a gel carrier, wherein the ultrasound reflective element and the at least one contrast material are carried in or on the gel carrier. The method also comprises detecting the target site and the composite gel marker with ultrasound imaging or a detection modality capable of detecting the at least one contrast material.

All above descriptions and embodiments discussed in the above aspect relating to the composite marker 100, including descriptions and embodiments relating to ultrasound reflective element 102, at least one contrast material 103, and gel carrier 104, are all applicable a method marking a target site in a mammalian subject.

In some embodiments, the target site comprises a tumor. The method further comprises surgically excising the tumor using ultrasound imaging or the detection modality capable of detecting the at least one contrast material as a detecting guidance, wherein the detecting guidance is different than the detection modality used in the detecting the target site and the composite gel marker.

A method of marking a target site in a mammalian subject may comprise: administering parenterally to the mammalian subject a composite marker, comprising: an activated and/or hydrolyzed fluorescent dye; at least one contrast material detectable by a detection modality different than detection of fluorescence; and a gel carrier, wherein the activated and/or hydrolyzed fluorescent dye and the at least one contrast material are carried in or on the gel carrier. The method also comprises detecting the target site and the composite gel marker with a detection modality that detects fluorescence or a detection modality different than detection of fluorescence and capable of detecting the at least one contrast material.

All above descriptions and embodiments discussed in the above aspect relating to the composite marker 400, including descriptions and embodiments relating to the fluorescent dye 403, the at least one contrast material 402, and the gel carrier 404, are all applicable to a method marking a target site in a mammalian subject.

In some embodiments, the target site comprises a tumor. The method further comprises surgically excising the tumor using a detection modality that detects fluorescence or the detection modality different than detection of fluorescence and capable of detecting the at least one contrast material as a detection guidance, wherein the detection guidance is different than the detection modality used in the detecting the target site and the composite gel marker.

In a method of marking a target site in a mammalian subject, the composite marker may be administered to the target site in a mammalian subject parenterally via any administration route known to one skilled in the art. For instance, parenteral administration of the composite marker can be performed by injection, for example, by using a needle and a syringe, or by the insertion of an indwelling catheter. In this case, the size and shape of the composite marker can be adjusted to fit in the internal size and shape of the needle, syringe, or catheter. More detailed descriptions about specific techniques that may be used for administering and delivering a gelatin marker to a tissue and suitable applicators may be found, for example in U.S. patent application Ser. No. 15/946,479, which is incorporated herein by reference in its entirety.

Unless otherwise indicated, use of the term "detecting" or "detection of" a composite marker herein refers to recognition of a return signal from a composite marker that is distinct from a return signal of tissue (or other material) at the target site surrounding or adjacent to the composite marker. For example, direct visual detection of a composite marker may include the ability of an observer to see the composite marker relative to the surrounding tissue due to a difference in color or fluorescence contrast, for example, between the marker and the surrounding tissue. A composite marker detected by ultrasound may reflect an ultrasound signal that is distinct in intensity, wavelength, phase, etc., relative to an ultrasound signal reflected by tissue surrounding or adjacent such a composite marker. In addition, effective detection in many cases does not need to include image projection onto a display screen for viewing by an operator such as is typically the case with fluoroscopic, ultrasonic, and magnetic resonance imaging (MRI). Detection of a composite marker may include reflection or return of some type of an energetic signal by the composite marker that may be projected from multiple points of origin to specify the location of a composite marker in three-dimensional space by methods such as triangulation. Such a technique may provide location information of the composite marker relative to the position of the multiple points of origin of the energetic signal. With regard to audio detection, an audible sound may be configured to increase in pitch, intensity, frequency or the like as a function of a probe's proximity to a composite marker and/or such a probe's appropriate directionality with respect to a composite marker.

In some instance, the composite marker may be detected by two or more different detection modalities. Certain detection modalities, such as fluoroscopy, computed tomography (CT) imaging, and/or MRI, are used by a specialist such as a radiologist to identify the location of the tissue lesion. Certain different detection modalities, such as visual imaging (direct viewing of the markers by color or fluorescence) and/or ultrasound imaging (e.g., color flow Doppler ultrasound imaging) may be used by a specialist such as a surgeon to facilitate the subsequent therapeutic procedure, possibly during surgical removal or other type of treatment of the tissue lesion. Certain different detection modalities may be used to evaluate excised tissue after surgical removal from the patient or for any other suitable indication.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

The teachings of U.S. patent application Ser. No. 62/941,336, filed Nov. 27, 2019 and entitled "COMPOSITE TISSUE MARKERS DETECTABLE VIA MULTIPLE DETECTION MODALITIES"; Ser. No. 62/941,337, filed Nov. 27, 2019 and entitled "COMPOSITE TISSUE MARKERS DETECTABLE VIA MULTIPLE DETECTION MODALITIES INCLUDING RADIOPAQUE WIRE"; U.S. patent application Ser. No. 63/073,285, filed Sep. 1, 2020 and entitled "COMPOSITE TISSUE MARKERS DETECTABLE VIA MULTIPLE DETECTION MODALITIES INCLUDING RADIOPAQUE ELEMENT"; and U.S. patent application Ser. No. 15/946,479, are incorporated herein by reference in their entirety.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

We claim:

1. A composite marker, comprising:
   a plurality of sealed ultrasound reflective elements, each ultrasound reflective element respectively comprising a porous body having an irregular outer surface, at least one cavity and at least one gas in the at least one cavity to provide reflectivity of ultrasound imaging signals, wherein each ultrasound reflective element comprises a hydrophobic coating that at least temporarily seals the at least one cavity thereof to retain the gas therein, wherein the hydrophobic coating comprises a mono-, di-, tri-, or tetra-alkoxysilane;
   at least one contrast material detectable via a detection modality different than ultrasound imaging, wherein the at least one contrast material is not included in an outer layer of each ultrasound reflective element; and
   a gel carrier that is at least partially crosslinked, wherein the plurality of sealed ultrasound reflective elements and the at least one contrast material are carried in or on the gel carrier.

2. The composite marker of claim 1, wherein each sealed ultrasound reflective element is formed of a shell having an outer wall that forms one cavity of the at least one cavity or a porous particle having more than one cavity of the at least one cavity, wherein the shell or porous particle comprises silica or titanium dioxide.

3. The composite marker of claim 2, wherein the shell or porous particle is silica shell or silica particle.

4. The composite marker of claim 1, wherein the at least one contrast material includes two or more different contrast materials, each detectable by a respective detection modality that is different from one another and different from ultrasound imaging.

5. The composite marker of claim 1, wherein the at least one contrast material is carried in or on the gel carrier in a colloidal dispersion therein.

6. The composite marker of claim 5, wherein the plurality of sealed ultrasound reflective elements and the at least one contrast material are carried in or on the gel carrier in a colloidal dispersion therein.

7. The composite marker of claim 1, wherein the at least one contrast material includes a radiopaque material, detectable via X-ray imaging.

8. The composite marker of claim 7, wherein the radiopaque material is a radiopaque metal selected from the group consisting of stainless steel, platinum, gold, iridium, titanium, tantalum, tungsten, silver, rhodium, nickel, bismuth, and barium; an alloy of the radiopaque metals; an oxide of the radiopaque metals; a sulfate of the radiopaque metals; a carbonate of the radiopaque metals; or a combination thereof.

9. The composite marker of claim 1, wherein the at least one contrast material includes at least one of: a dye or a pigment, visually detectable.

10. The composite marker of claim 9, wherein the at least one contrast material includes at least one of: a pigment, a visible dye, a fluorescent dye, a near-infrared dye, or an ultraviolet (UV) dye.

11. The composite marker of claim 10, wherein the at least one contrast material includes at least one of: methylene blue, indigo dye, or indocyanine green.

12. The composite marker of claim 1, wherein the at least one contrast material includes at least one of: a paramagnetic, superparamagnetic, ferrimagnetic or ferromagnetic compound, or a compound containing other non-zero spin nuclei than hydrogen, detectable via magnetic resonance imaging (MRI).

13. The composite marker of claim 12, wherein the at least one contrast material includes at least one of: a manganese or manganese-based compound; a gadolinium or gadolinium-based compound; or ferrous gluconate, ferrous sulfate, iron oxide, or iron platinum.

14. The composite marker of claim 1, wherein the at least one contrast material contains a radioactive material, detectable via nuclear-based imaging.

15. The composite marker of claim 1, wherein the gel carrier comprises a natural gelatinous material, a synthetic polymer, or a combination thereof.

16. The composite marker of claim 15, wherein the gel carrier comprises:
   i) a protein selected from the group consisting of collagen, gelatin, fibrin, fibronectin, and albumin;
   ii) a polysaccharide selected from the group consisting of cellulose or methyl cellulose, hyaluronic acid, chitin, chitosan, and calcium alginate;
   iii) a synthetic polymer selected from the group consisting of polyvinyl alcohol (PVA), polyglycolic acid (PGA), polylactic acid (PLA), poly(glycolic-co-lactic acid) (PLGA), polycaprolactone (PCL), polymethacrylate (PMA), polymethylmethacrylate (PMMA), polyethylene oxide (PEO), polyamine, polyoxaamide, polyoxaester, polyethylene glycol (PEG), polypropylene (PP), polytetrafluoroethylene (PTFE), polyester, polyetheretherketone (PEEK), and a copolymer thereof; or
   a mixture of any two or more members from i), ii), or iii).

17. The composite marker of claim 15, wherein the gel carrier is at least partially crosslinked, via a physical process, a chemical modification, and/or using a crosslinking agent.

18. The composite marker of claim 17, wherein the gel carrier is rendered at least partially crosslinked by using a crosslinking agent selected from the group consisting of an aldehyde, glutaraldehyde, glyceraldehyde, dialdehyde, starch, epoxide, dimethyl adipimidate, glucosepane, carbodiimide, pentosidine, isocyanate or polyisocyanate, metallic crosslinker, ionic crosslinker, acrylic compound, alginate, sulfhydryl, genipin, and a combination thereof.

19. The composite marker of claim 17, wherein the gel carrier is rendered at least partially crosslinked by freezing and/or thawing.

20. The composite marker of claim 17, wherein a degree of crosslinking of the gel carrier is pre-determined by a rate of degradation of the gel carrier a tissue of a host mammalian subject.

21. The composite marker of claim 20, wherein the rate of degradation of the gel carrier in the tissues of the host mammalian subject is such that the gel carrier persists in the tissues of the host mammalian subject for a period of at least three weeks, and optionally for a period of about 9 months or longer.

22. The composite marker of claim 1, wherein the mono-, di-, tri-, or tetra-alkoxysilane of the hydrophobic coating is selected from: the group consisting of: propyltrimethoxysilane, hexyltrimethoxysilane, heptyltrimethoxysilane, octyltrimethoxysilane, nonyltrimethoxysilane, decyltrimethoxysilane, dodecyltrimethoxysilane, tridecyltrimethoxysilane, tetradecyltrimethoxysilane, pentadecyltrimethoxysilane, hexadecyltrimethoxysilane, heptadecyltrimethoxysilane, octadecyltrimethoxysilane, phenyltrimethoxysilane, propyltriethoxysilane, hexyltriethoxysilane, heptyltriethoxysilane, octyltriethoxysilane, nonyltriethoxysilane, decyltriethoxysilane, dodecyltriethoxysilane, tridecyltriethoxysilane, tetradecyltriethoxysilane, pentadecyltriethoxysilane, hexadecyltriethoxysilane, heptadecyltriethoxysilane, octadecyltriethoxysilane, phenyltriethoxysilane, methoxy (triethyleneoxy) propyltrimethoxysilane, 3-(methacryloyloxy) propyltrimethoxysilane, m, p-ethylphenethyltrimethoxysilane, 2-[methoxy (polyethyleneoxy) propyl]-trimethoxysilane, 3-aminopropyltrimethoxysilane, 3-mercaptopropyltrimethoxysilane, 3-isocyanatopropyltriethoxysilane, 3-isocyanatopropyltrimethoxysilane, and glycidoxypropyltrimethoxysilane.

23. The composite marker of claim 1, wherein the at least one contrast material includes an activated and/or fluorescent dye or a pigment that is visually detectable and that is carried in or on the gel carrier.

* * * * *